United States Patent [19]

Green et al.

[11] Patent Number: 4,608,973

[45] Date of Patent: * Sep. 2, 1986

[54] PATIENT RESTRAINING DEVICE

[76] Inventors: Frank H. Green, 516 N. Morgan St., Rushville, Ind. 46173; David L. Green, 20 Oakshore Dr., Bratenahi, Ohio 44108

[*] Notice: The portion of the term of this patent subsequent to Nov. 29, 2000 has been disclaimed.

[21] Appl. No.: 573,692

[22] Filed: Jan. 25, 1984

[51] Int. Cl.$^4$ .............................................. A61F 31/00
[52] U.S. Cl. ...................................... 128/134; 340/668
[58] Field of Search .................. 128/133, 134; 340/668

[56] References Cited

U.S. PATENT DOCUMENTS

| | | | |
|---|---|---|---|
| 1,699,663 | 1/1929 | Hess | 340/548 |
| 2,036,171 | 3/1936 | Fox | 369/24 |
| 2,478,239 | 8/1949 | Chinn | 128/134 |
| 2,751,594 | 6/1956 | Brissenden | 128/134 X |
| 3,265,065 | 8/1966 | Jillson | 128/134 |
| 3,638,647 | 2/1972 | Creelman | 340/668 |
| 3,641,997 | 2/1972 | Posey | 128/134 |
| 3,670,320 | 6/1972 | Palmer | 340/573 |
| 4,007,733 | 2/1977 | Celeste et al. | 128/781 |
| 4,263,586 | 4/1981 | Nicholas | 200/85 R |
| 4,360,014 | 11/1982 | Manahan | 128/134 |

FOREIGN PATENT DOCUMENTS 569490  1/1959  Canada .............................. 128/134

Primary Examiner—Dalton L. Truluck
Assistant Examiner—Karen Kaechele
Attorney, Agent, or Firm—Woodard, Weikart, Emhardt & Naughton

[57] ABSTRACT

Disclosed is an open-back restraining vest having posterior wings which overlap in back to close the vest. Attached to the end of each posterior wing is a tie-strap, one of which is disposed through a loop on the exterior of the other posterior wing, the other tie-strap being disposed through a slot in the first posterior wing, whereby the application of tension to the tie-straps serves to draw the vest closed. The tie-straps are anchored to the rails of a bed, the amount of slack determining the limits of the patient's range of movement. Additional monitor straps attached to the vest may be connected to an alarm to indicate when the patient is approaching the limit of his permissible range of movement.

1 Claim, 6 Drawing Figures

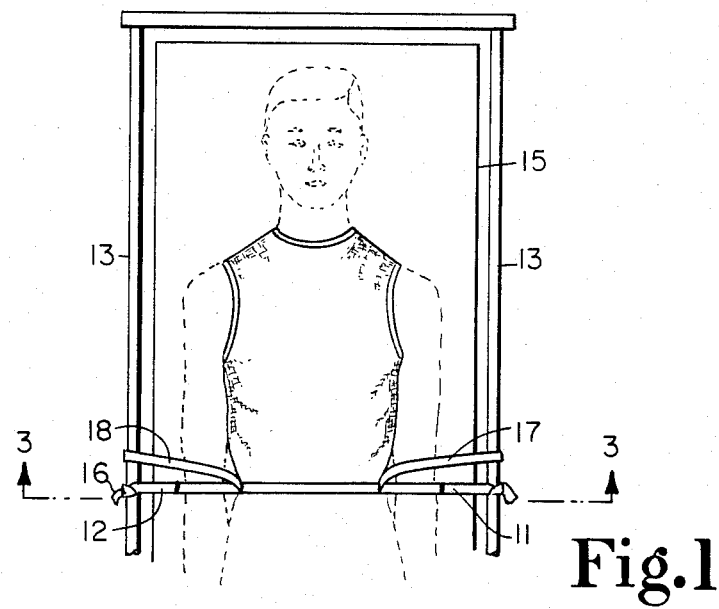
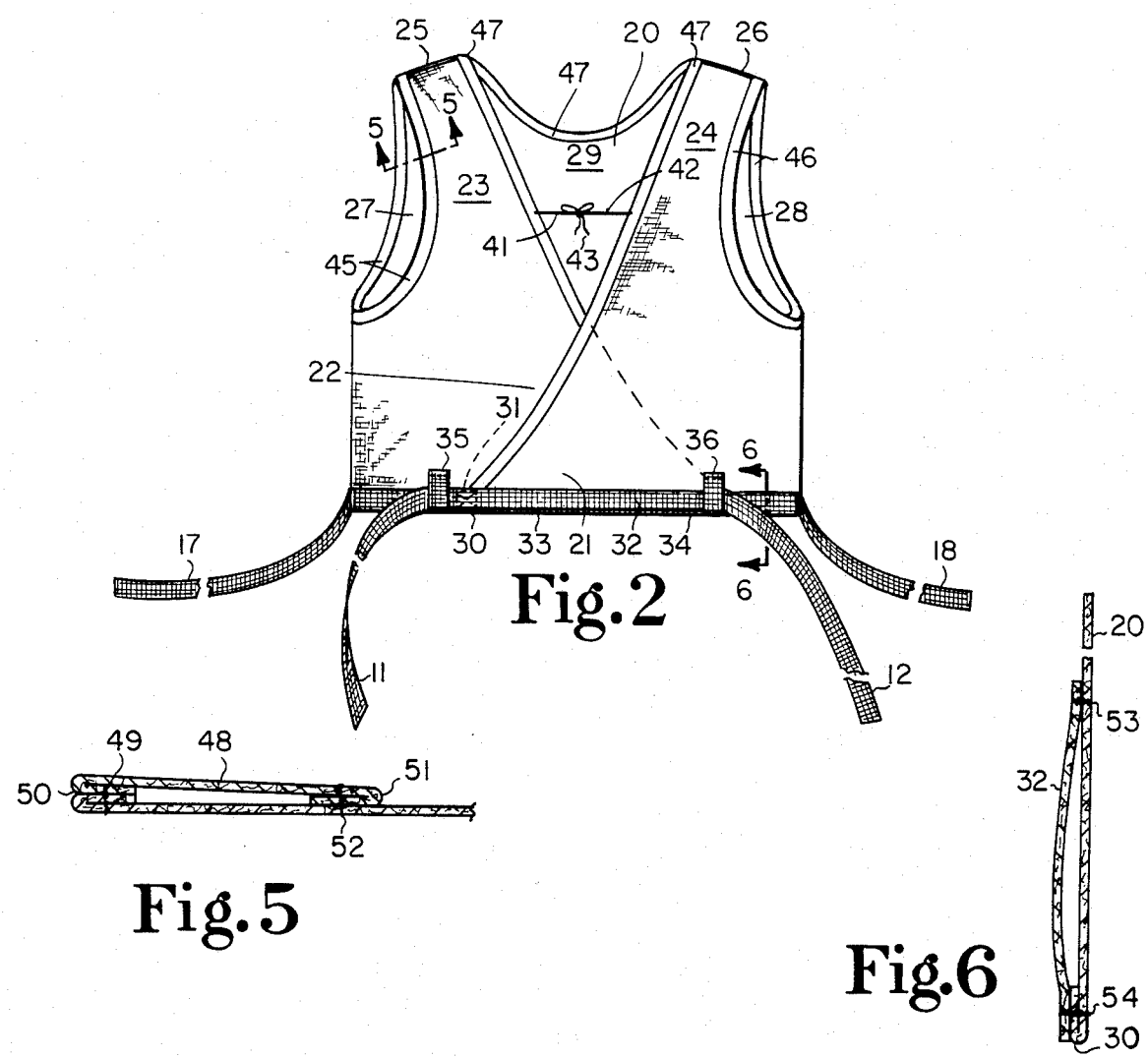

PATIENT RESTRAINING DEVICE

BACKGROUND OF THE INVENTION

1. Field of the Invention:

This invention relates to a device for restraining a patient in bed which is particularly adapted for use with a monitoring device.

2. Description of the Prior Art:

Various devices have been employed to restrain a patient in bed while allowing limited movement. One such device is disclosed in U.S. Pat. No. 3,236,234, issued to Buckley on Feb. 22, 1966. Buckley shows a wide band of fabric-like material which encircles the waist of the patient and which is closed in back by means of zippers, hooks and snaps. Attached to the band are straps which are tied to the rails of the bed to limit the patient's range of motion. Another such device is disclosed in U.S. Pat. No. 3,182,338, issued to Shirrod on May 11, 1965. Shirrod shows a belt having an elongated slot intermediate its ends. One end of the belt is wrapped around the patient and then passed through the elongated slot. The ends of the belt are wrapped around the bed rails and then buckled together beneath the bed.

One problem associated with devices such as that shown in Buckley is the lack of adjustability of the band to fit persons of different sizes. Another problem is that it is fairly expensive to manufacture a device using zippers, snaps and hooks as a closure means.

The Shirrod device by its nature solves the problem of adjustability, but suffers from different problems. Being a narrow belt, Shirrod's device is likely to be uncomfortable. Any pressure or friction that might occur is concentrated on a small area of the patient's body. The belt is also subject to being removed by the patient by slipping it down over the hips and legs.

A device which is adapted for use with a conventional strap restraint and which further provides an alarm to indicate excessive movement of the patient is described in U.S. Pat. No. 4,417,572, issued to Green on Nov. 29, 1983. The Green device is normally effective in alerting monitoring personnel of a patient's excessive movement, but its effectiveness can be negated if the restraining belt to which it is attached slips off of or is removed by the patient.

Thus, it would be desirable to provide a restraining device which is inexpensive, is adjustable to fit persons of various sizes, does not cause excessive localized irritation, is not easily removed by the patient and may be used to improve the effectiveness of a monitoring device.

SUMMARY OF THE INVENTION

One embodiment of the present invention involves a restraining vest for restraining a patient in bed. The vest, having an open back, is configured to be received about the upper body of the patient. The vest has a first posterior wing and a second posterior wing, each posterior wing configured to be disposed at the back of the patient and each having a tie-strap attached thereto. The first posterior wing has an exterior loop affixed thereto and the second posterior wing defines a slot therethrough. The tie-strap of the first posterior wing is disposed through the slot of the second posterior wing and the tie-strap of the second posterior wing is disposed through the loop of the first posterior wing. The tie-straps serve to draw the vest closed about the patient and, when anchored to the bed, serve to limit the range of movement of the patient.

Another embodiment of the present invention involves the cmbination of the above-described vest with a patient excessive movement monitoring device. The vest is provided with monitor straps which are attached to the monitoring device. In use, the monitor straps are configured with less slack than the tie-straps so that the monitoring device will activate an alarm before the patient reaches the limit of his permissible range of movement.

It is an object of the present invention to provide a vest for restraining a patient in bed.

It is another object of the present invention to provide a restraining vest which is inexpensive to manufacture.

It is another object of the present invention to provide a restraining vest having a unique closure which is adjustable to fit persons of various sizes and which also serves as the restraining means.

It is a further object of the present invention to provide a restraining vest which is not easily removed by the patient.

It is a still further object of the present invention to provide a restraining vest configured for use with a monitoring device to activate an alarm before a restrained patient reaches the limit of his permissible range of movement.

Other objects and advantages of the present invention will be apparent from the following description.

BRIEF DESCRIPTION OF THE DRAWINGS

FIG. 1 is a plan view of the restraining vest of the present invention in use.

FIG. 2 is an elevational view of the restraining vest of the present invention, showing the vest from the back.

FIG. 5 is a detail sectional view of one of the seams of the restraining vest taken substantially upon a plane passing through section line 5—5.

FIG. 6 is a detail sectional view of one of the seams of the restraining vest taken substantially upon a plane passing through section line 6—6.

DESCRIPTION OF THE PREFERRED EMBODIMENT

Figure 3:
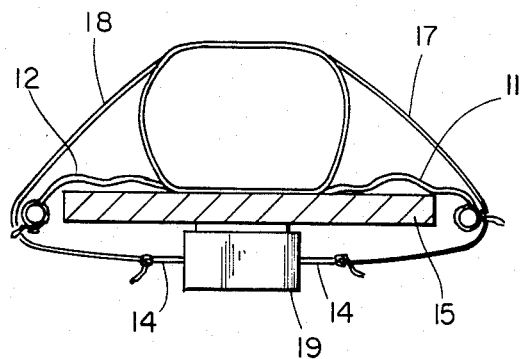
FIG. 3 is a sectional view taken substantially upon a plane passing through section line 3—3.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring in particular to FIGS. 1 and 2, there is shown the vest 10 of the present invention. Vest 10 has an open back and is configured to be disposed about the upper body of a patient who is to be restrained in bed. Important components of vest 10 are tie-straps 11 and 12, which serve somewhat like draw-strings to close vest 10 in the back and draw it up snugly against the patient's body. Tie-straps 11 and 12 also serve to restrain the patient to a bed 15, the tie-straps being anchored to the side-rails 13 of bed 15 by a knot 16 or other suitable fastening means, such as a buckle. The amount of slack remaining in tie-straps 11 and 12 after being anchored to rails 13 determines the limits of the patient's range of movement.

Attached to vest 10 are monitor straps 17 and 18, which are preferably connected to a monitoring device 19 (FIG. 3) located beneath bed 15 that detects and indicates by an alarm excessive movement of the patient. Monitor 19 includes a movable member 14, to which monitor straps 17 and 18 are attached. Movement of movable member 14 beyond a predetermined limit activates the alarm (alarm not shown). Such a monitor is described in U.S. Pat. No. 4,417,572, issued to Green on Nov. 29, 1983. In use, monitor straps 17 and 18 are provided with less slack than tie-straps 11 and 12, thus insuring that the excessive movement monitor 19 will be activated before the patient reaches the limit of his permissible range of movement. A nurse or other monitoring personnel will therefore be alerted before the patient is in any danger of falling out of bed or otherwise harming himself by excessive movement.

Figure 4:
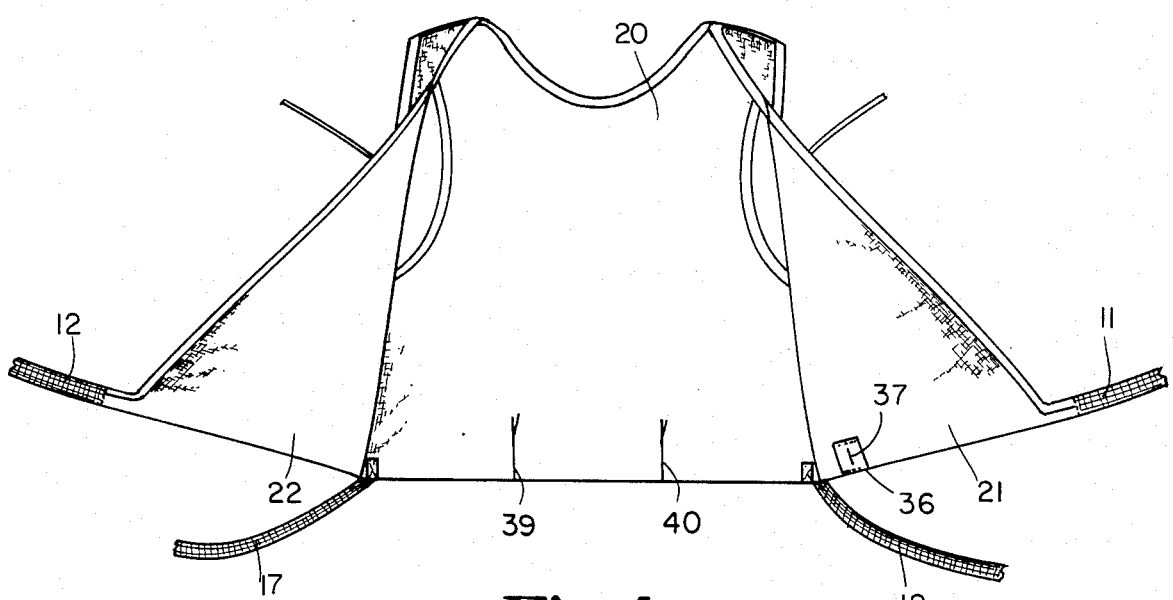
FIG. 4 is an elevational view of the interior of the restraining vest, particularly showing the darts in the front panel and the reinforced slot in one of the posterior wings.

Vest 10 includes a front panel 20 which covers the patient's chest. Front panel 20 is provided with darts 39 and 40 (FIG. 4) stitched therein to provide a slight taper at the waist of the vest. Integral with front panel 20 are posterior wings 21 and 22 which overlap in back to close the vest. Posterior wings 21 and 22 have integral shoulder straps 23 and 24 which are sewed at 25 and 26 to front panel 20, thus forming arm holes 27 and 28 and neck opening 29. Vest 10 may be of any cloth-like fabric, although cotton or a cotton-polyester blend is preferred.

The bottom edge 30 of vest 10 is provided with a belt 32 of woven cloth-like material having a high tensile strength. Belt 32 is sewed to vest 10 continuously along its length. The ends of belt 32 extend beyond ends 33 and 34 of posterior wings 21 and 22 to form integral tie-straps 11 and 12. Multiple stitching, as shown at 31, is employed to reinforce the point of connection between tie-straps 11 and 12 and ends 33 and 34.

Posterior wing 22 is provided with a strip 35 of the same material as belt 32, which is sewn at its top and bottom ends to the underlying fabric of posterior wing 22 to form a loop through which tie-strap 11 is disposed. A similar strip 36 is provided on posterior wing 21, although strip 36 serves only to conceal the underlying slot 37 (FIG. 4) which is provided in posterior wing 21. Tie-strap 12 is disposed through slot 37 from the interior of the vest to the exterior. A strip 44 is provided on the interior surface of panel 20 to reinforce slot 37.

The posterior wings 21 and 22 are provided with tie-cords 41 and 42 at the mid-scapular line, which may be tied together in a bow knot 43 to give additional support to vest 10 to help prevent it from being removed by slipping it over the shoulders.

Referring in particular to FIG. 5, there is shown the detail of the construction of armhole seams 45 and 46, and neck opening seam 47. One edge of a cloth finishing strip 48 is stitched to the edge of the vest fabric at 49. The seam is then reverse folded at 50 with the other edge of strip 48 being reverse folded at 51 and stitched at 52 to provide a neat, ravel free finished seam.

Referring in particular to FIG. 6, there is shown the detail of the construction of the seam at bottom edge 30 of vest 10. The vest fabric is reverse folded at edge 30 and belt 32 is stitched to panel 20 along its edges at 53 and 54.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A patient restraint device for use by a patient to be restrained on a bed against excessive vertical and horizontal movement with respect to said bed, and for alerting nursing personnel of impending excessive movement before said patient is endangered thereby, comprising:

a vest securely received about the upper body of said patient;

an alarm;

bidirectional alarm activating switch means located beneath and fixed to said bed out of reach of the patient, and responsive to pulling force applied thereto in either of two opposite horizontal directions, for activating said alarm in response to pulling force exceeding a predetermined limit applied in any of said opposite horizontal directions;

means for translating vertical or horizontal motion of said patient into pulling force applied in at least one of said opposite first and second horizontal directions, said translation means including:

a first monitor strap having first and second ends, the first end securely attached to said vest, said first strap extending from said vest over one side of said bed, the second end thereof connected to said bidirectional alarm activating switch means such that tension in said first monitor strap exerts a pulling force in the first direction; and a second monitor strap having first and second ends, the first end securely attached to said vest, said second strap extending from said vest over the other side of said bed, the second end thereof connected to said bidirectional alarm activating switch means such that tension in said second monitor strap exerts a pulling force in the second direction.

* * * * *